United States Patent [19]

Gardlik et al.

[11] Patent Number: 5,106,999
[45] Date of Patent: Apr. 21, 1992

[54] PROCESS FOR PREPARING DIBENZYLIDENE-D-SORBITOL COMPOUNDS

[75] Inventors: John M. Gardlik; Raymond V. Burkes, both of Cincinnati, Ohio

[73] Assignee: The Procter & Gamble Company, Cincinnati, Ohio

[21] Appl. No.: 543,943

[22] Filed: Jun. 26, 1990

[51] Int. Cl.$^5$ .......................................... C07D 319/04
[52] U.S. Cl. ................................................... 549/364
[58] Field of Search .......................................... 549/364

[56] References Cited

U.S. PATENT DOCUMENTS

| | | | |
|---|---|---|---|
| 4,131,612 | 12/1978 | Uchiyama | 260/340.7 |
| 4,154,816 | 5/1979 | Roehl et al. | 424/68 |
| 4,429,140 | 1/1984 | Murai et al. | 549/370 |
| 4,518,582 | 5/1985 | Schamper et al. | 424/66 |
| 4,562,265 | 12/1985 | Machell | 549/364 |
| 4,743,444 | 5/1988 | McCall | 424/65 |
| 4,816,261 | 3/1989 | Luebbe et al. | 424/65 |

FOREIGN PATENT DOCUMENTS 0286522 10/1988 European Pat. Off. .
1-62377 3/1989 Japan .

*Primary Examiner*—Nicky Chan
*Attorney, Agent, or Firm*—John M. Howell; Steven J. Goldstein; Richard C. Witte

[57] ABSTRACT

A process for preparing dibenzylidene-D-sorbitol compounds, particularly meta substituted halogenated derivatives, by reacting D-sorbitol with an aromatic aldehyde, particularly those substituted at the 3 position with a halogen, in the presence of an acid catalyst, and a $C_1$–$C_3$ aliphatic alcohol reaction medium. The resulting product is purified by subsequent washings with a $C_1$–$C_3$ aliphatic alcohol. Higher yields of the product, shorter reaction times, and simplified removal of impurities may be realized using this invention.

16 Claims, No Drawings

PROCESS FOR PREPARING DIBENZYLIDENE-D-SORBITOL COMPOUNDS

FIELD OF THE INVNETION

The present invention relates to the preparation of dibenzylidene-D-sorbitol compounds, such as those which are substituted at the meta positions. This process can provide advantages over the art in terms of yield and purity of the product, as well as efficiency of the process itself. The resulting compounds may be used as gelling agents for solid gel antiperspirant and deodorant sticks.

BACKGROUND OF THE INVENTION

Hard soap/alcohol gel sticks make desirable application vehicles for cosmetics and deodorants because they tend to exhibit good skin glide and low visible residue. Unfortunately, the acidic antiperspirant actives interfere with the gel structure and render it less cosmetically desirable.

Acceptable cosmetic and deodorant gel sticks may, however, be made using dibenzylidene sorbitol (DBS) and certain of its derivatives as the gelling agent, instead of soap. DBS gel sticks are disclosed in U.S. Pat. No. 4,154,816, Roehl et al., issued May 15, 1979; U.S. Pat. No. 4,518,582, Schamper et al., issued May 21, 1985; U.S. Pat. No. 4,743,444, McCall, issued May 10, 1988; and U.S. Pat. No. 4,816,261, Luebbe et al., issued Mar. 28, 1989; all incorporated herein by reference. Japanese Published Application 64-62377, Kao, published Mar. 8, 1989, describes fluorinated dibenzylidene polyhydric alcohol derivatives, including sorbitols, as effective gelling agents for cosmetic compositions containing a wide range of organic solvents.

Specific methods for making DBS are disclosed in U.S. Pat. No. 4,429,140, Murai et al., issued Jan. 31, 1984, and European Patent Application 0286522, Salome et al., published Jan. 12, 1988; both incorporated herein by reference. Murai et al. discloses a method for producing DBS and its derivatives using substituted or unsubstituted benzaldehyde and alkyl acetal derivatives of benzaldehyde, sorbitol, an acid catalyst, a hydrophobic solvent reaction medium (e.g., cyclohexanes, carbon tetrahalides, aromatic hydrocarbons, hydrocarbon halides, and nitro compounds), and a hydrophilic organic polar solvent (e.g., alcohols and glycol ethers). The reaction is a dehydration/condensation process in which the water and hydrophobic solvent azeotrope is continuously removed. The presence of sufficient amounts of the hydrophobic solvent is necessary for the DBS to precipitate out. Furthermore, the hydrophilic solvent solubilizes both the sorbitol and aldehyde, which is necessary for the reaction to proceed. In this process the hydrophilic and hydrophobic solvents must be carefully balanced, making it rather complex and costly. Furthermore, a complicated recycling process for the hydrophobic solvent is disclosed therein.

U.S. Pat. No. 4,131,612, Uchiyama, issued Dec. 26, 1978, discloses the use of lower aliphatic alcohols, such as methanol, for purifying crude DBS made by a process similar to Murai et al. (i.e., where cyclohexane is used as the solvent medium). In this purification process, a solution of crude DBS and methanol is heated to at least 50° C. to remove mono- and tribenzylidene-D-sorbitols which account for up to 7% by weight of the crude DBS. However, as is the case in Murai et al., using cyclohexane, a hydrophobic organic solvent, makes the process quite complicated.

An alternative process to Murai et al. for producing DBS is disclosed in European Patent Application No. 0286522, Salome et al., published Oct. 12, 1988. Salome et al., like the references above, utilizes an acetalization reaction catalyzed by an argylsulfonic acid to yield, upon successive dehydration, dibenzylidene-D-sorbitol compounds, including the para-chlorine derivatives. This process utilizes an aqueous medium instead of the hydrophobic organic solvent eliminating the steps surrounding reclamation of the solvent reaction medium as taught by Murai et al.. Furthermore, the hydrophilic organic co-solvent is eliminated making the reaction relatively simple.

The Salome et al. process, however, requires neutralization of the residual acid catalyst. Omission of the neutralization step results in formation of DBS isomers which will not gel. Neutralization, however, leaves alkaline impurities in the product which causes chemical reactions among other ingredients in the stick formulation, thereby depleting the gellant. In addition to the neutralization problem, halogenated, specifically chlorinated, DBS derivatives are not preferred for manufacturing using the Salome et al. process due to the low yield of DBS and the high yield of monobenzylidene-D-sorbitol compound.

While the reaction parameters of the present invention, such as the molar ratios of aromatic aldehyde to D-sorbitol, the use of aryl sulfonic acid catalysts, and the molar ratio of acid and aromatic aldehyde, are similar to those taught in the art, the process of the present invention utilizes a $C_1$-$C_3$ aliphatic alcohol, as opposed to a hydrophobic solvent or water, as the reaction medium. Using the alcohol instead of a dual solvent as in Murai et al. simplifies the reaction. Subsequent washing with the alcohol effectively removes the acid catalyst without neutralization as taught by Salome et al., eliminating alkaline impurities in the product. Furthermore, residual alcohol is quickly removed from the product of the present invention by simple means, such as drying in air or in an oven, whereas the removal of the water from the product of the Salome et al. process, is more difficult. In addition, eliminating water from gel sticks gene-rally results in better cosmetics.

The present process, therefore, produces, in a simple manner, dibenzylidene sorbitol compounds, and particularly meta-substituted halogenated derivatives, which have better purity when compared to materials made by processes taught in the art. Better purity means that the DBS compounds are essentially free of water, hydrophobic organic solvents (such as cyclohexane), undesirable mono- and tribenzylidene sorbitol compounds, acid catalyst, and alkaline impurities. Products made by this process have superior properties when used as gelling agents in antiperspirant stick compositions.

All parts and percentages given herein are by weight unless otherwise indicated.

SUMMARY OF THE INVENTION

The present invention provides a process for making dibenzylidene-D-sorbitol compounds consisting essentially of the steps of:

a. combining D-sorbitol, an aromatic aldehyde, an acid catalyst, and a $C_1$-$C_3$ aliphatic alcohol reaction medium;

b. allowing the mixture to form a thick paste; and c. purifying the resulting dibenzylidene-D-sorbitol compound formed using a $C_1$–$C_3$ aliphatic alcohol until the compound is substantially free of the acid catalyst;

wherein the initial molar ratio of the aromatic aldehyde to the D-sorbitol is from about 1:1 to about 2:1, preferably from about 1.5:1 to about 1.9:1, and most preferably from about 1.7:1 to about 1.8:1, and the initial molar ratio of the acid catalyst to the aromatic aldehyde is from about 0.6:1 to about 1.5:1, preferably from about 0.6:1 to about 1:1, and most preferably about 0.7:1.

The components listed in (a) above may all be added together in a single step or added in premixed combinations, for example, D-sorbitol may be premixed with the aliphatic alcohol.

The process disclosed herein can produce dibenzylidene-D-sorbitol compounds having better purity, with greater yields in shorter periods of time, than the processes taught in the art. Specifically, the products of the present process are substantially free of the acid catalyst, water, mono- and tribenzylidene sorbitols, and alkaline impurities (such as sodium hydroxide, sodium carbonate, and sodium bicarbonate). This allows for easier processing and more flexible formulation when these DBS products are used in gel sticks.

The process of the present invention is especially useful in making meta-halogenated dibenzylidene-D-sorbitol compounds, such as di-(meta-fluorobenzylidene)-D-sorbitol. In making these compounds, the aromatic aldehyde used herein is substituted with a halogen at the 3 position.

DETAILED DESCRIPTION OF THE INVENTION

The process of the present invention is for the production of dibenzylidene-D-sorbitol compounds having the structure:

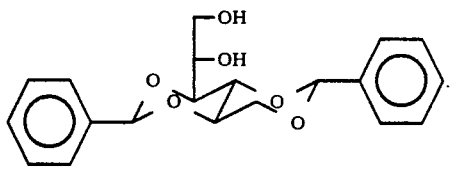

It is particularly useful for the synthesis of meta-halogenated dibenzylidene-D-sorbitol compounds having the structure

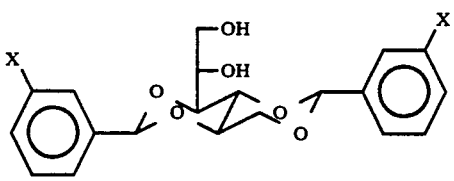

wherein X is located at the meta position and is selected from the group consisting of fluorine, chlorine and bromine. The process for preparing DBS compounds involves combining D-sorbitol, an aromatic aldehyde, an acid catalyst, and a $C_1$–$C_3$ aliphatic alcohol reaction medium. The DBS compounds formed are washed with an additional amount of a $C_1$–$C_3$ aliphatic alcohol to remove essentially all the acid catalyst. In order to synthesize the meta halogenated DBS derivatives, aromatic aldehydes having a halogen substituent at the 3 position are utilized in the reaction. This process for making dibenzylidene-D-sorbitol compounds removes the acid catalyst without neutralization resulting in DBS compounds useful in making gel stick antiperspirant and deodorant compositions. Removal of the acid is thought to prevent rearrangement or hydrolysis reactions of the DBS which form non-gelling compounds such as 1,3:4,6-dibenzylidene-D-sorbitol. Accomplishing this without leaving alkaline impurities via neutralization also avoids chemical reactions among the stick's components, due to the presence of the base, which depletes the gel. This process also minimizes less desirable mono- and tribenzylidene-D-sorbitol compounds, as well as water, allowing the formation of gel sticks with good cosmetic properties.

The first step of the process involves mixing D-sorbitol, an aromatic aldehyde, an acid catalyst, and a $C_1$–$C_3$ aliphatic alcohol reaction medium. These ingredients may be added together at once or combined as premixes. For example, D-sorbitol can be mixed with the alcohol prior to the addition of the aldehyde and acid catalyst. As the mixture of alcohol and D-sorbitol is slightly endothermic, low heat may be applied to keep the mixture at about room temperature.

D-sorbitol is the hexahydric alcohol having the following formula

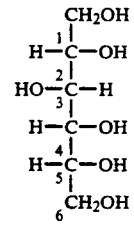

wherein the absolute configuration of the number 5 carbon atom has a hydroxyl group extending to the right.

The reaction medium is a $C_1$–$C_3$ aliphatic alcohol selected from the group consisting of methanol, ethanol, isopropanol, and mixtures thereof. It is desirable that the alcohol be absolute (i.e., that it contain substantially no water). The preferred alcohol for use in the present invention is absolute methanol. The alcohol reaction medium is present in an amount which is sufficient to solubilize the sorbitol with other reaction components and permit the reaction to proceed. Generally this will mean that the alcohol reaction medium is present in an initial weight ratio of alcohol to sorbitol from about 1:1 to about 20:1, preferably from about 2:1 to about 15:1, and most preferably from about 2.5:1 to about 3:1. The alcohol reaction medium may be added all at once, or may be added incrementally during mixing.

Substituted or unsubstituted aromatic aldehydes are required components in the reaction mixture disclosed herein. Such aromatic aldehydes are disclosed in U.S. Pat. No. 4,429,140, Murai et al., issued Jan. 31, 1984, and U.S. Pat. No. 4,562,265, Machell, issued Dec. 31, 1985, both incorporated herein by reference. Preferred aromatic aldehydes have a substituent selected from the group consisting of hydrogen, fluorine, chlorine, and bromine. Most preferred aromatic aldehydes have said substituents (designated as R) at the 3rd (meta) position and have the structure

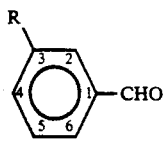

Such aromatic aldehydes include benzaldehyde, 3-fluorobenzaldehyde, 3-chlorobenzaldehyde, 3-bromobenzaldehyde, and mixtures thereof. The aromatic aldehyde is added to the reaction mixture at a level such that the molar ratio of aldehyde to sorbitol is from about 1:1 to about 2:1, preferably from about 1.5:1 to about 1.9:1, and most preferably from about 1.7:1 to about 1.8:1.

The acid catalyst facilitates the acetalization of D-sorbitol by the aromatic aldehyde. The acid catalyst is used at a level wherein the initial molar ratio of the acid catalyst to the aromatic aldehyde is from about 0.6:1 to about 1.5:1, preferably from about 0.6:1 to about 1:1, and most preferably about 0.7:1. The acid catalyst is an arylsulfonic acid selected from the group consisting of para-toluenesulfonic acid monohydrate, benzenesulfonic acid, 5-sulfosalicylic acid, naphthalenesulfonic acid, and mixtures thereof, as disclosed in European Patent Application 0286522, Salome et al., published Oct. 12, 1988. Preferred is para-toluenesulfonic acid monohydrate.

To facilitate the reaction, it is preferred that the solution of sorbitol, aldehyde, acid catalyst and alcohol be continuously stirred using a mechanical mixer, such as a 40 gallon double blade planetary mixer, until the reaction is completed, as indicated by the reaction mixture attaining a thick paste containing enough solid DBS such that, when it is scooped out with a spoon and placed on a flat surface, it does not run or separate into solid and liquid phases. The mixer utilized is one which can handle extremely viscous reaction mixtures. The stirring time is dictated by the efficiency of the equipment and volume of the material being processed, but will generally be in the range of from about 3 hours to about 48 hours. For example, when making about 14 kg of product in a 40 gallon double blade planetary mixer, stirring time is about 20 hours.

After completion of the reaction, the product is purified, or washed, by alcohol extraction using a $C_1$-$C_3$ alcohol. Specifically, to the paste is added an amount of a $C_1$-$C_3$ aliphatic alcohol having an initial weight ratio of alcohol to D-sorbitol from about 1:1 to about 50:1, preferably from about 2:1 to about 25:1, and most preferably from about 4:1 to about 10:1. The paste is stirred until all the alcohol is absorbed. The alcohols are selected from the group consisting of methanol, ethanol, isopropanol, and mixtures thereof; preferred is methanol. Although the above alcohols or mixture of alcohols used as the reaction medium do not necessarily have to be the same as that used for the purification step, it is preferred that they are the same.

The DBS/alcohol mixture is then poured into a filtering apparatus. The filter selected is dependent upon the scale of the production process. For example, on a relatively small scale, a large vacuum filter is used; the filtrate is pressed out through the filter using a rubber dam. On a large scale, the product can be filtered incrementally in one filter, or at one time in a number of filters.

After filtration, the solid product remaining in the filter is transferred back into a processing vessel where the above purification step, with the previously described $C_1$-$C_3$ aliphatic alcohol, is repeated. The mixture is stirred until the alcohol is absorbed by the product. Filtering and subsequent extractions with a $C_1$-$C_3$ aliphatic alcohol is repeated from about 3 to about 6 times until the product is substantially free of acid catalyst. Routine analytical methods, such as high performance liquid chromatography (HPLC) and proton nuclear magnetic resonance ($^1$NMR) indicate that the level of the acid catalyst is below 0.1% in the product made by the present process, however, the maximum level of acid which is acceptable has not been determined. An alternative test to determine if the acid level is low enough consists of heating a mixture of about 3.5% of the dried product in about 96.5% of propylene glycol to 120° C. for about 10 minutes. If too much aryl sulfonic acid is still present, a rearrangement reaction occurs in which the DBS compound is converted to other compounds which do not allow the gel to form adequately, and consequently the propylene glycol and dibenzylidene-D-sorbitol mixture remains a liquid upon cooling or forms a gel which is too soft for use as a stick composition. This indicates further purification is necessary to remove the acid. The formation of these non-gelling compounds can also be measured by HPLC analysis of this mixture.

The present method also significantly reduces formation of inferior gelling agents, such as mono- and tribenzylidene sorbitols, in the reaction product. The process disclosed herein is relatively simple, avoiding using a multitude of solvents which must be carefully balanced to allow the reaction to go forward and facilitate isolation of the product. Furthermore, the removal of the acid catalyst without neutralizations avoids alkaline impurities which causes chemical reactions among the other stick components which depletes the gel. Lastly, as gel sticks which minimize water have better cosmetics, replacing water as the reaction medium with the $C_1$-$C_3$ alcohol precludes extensive drying of the DBS. Drying the DBS may be accomplished by various methods such as air drying and oven drying. In the present invention, it is preferred that once the washing is completed, the filter cake is broken into small pieces and dried in air until hard lumps of white solid remain. These lumps are ground into a fine powder and dried until a constant weight is obtained.

The following examples illustrate the process of the present invention.

EXAMPLE 1

Preparation of di-(meta-fluorobenzylidene)-d-sorbitol

With stirring, add 621.2 g of D-sorbitol and 2 liters of absolute methanol to a 2 gallon, stainless steel, double blade planetary mixer. Add 763.2 g of 3-fluorobenzaldehyde and 811.4 g of para-toluenesulfonic acid monohydrate to the mixer and continue stirring for about 15 hours until a thick paste is formed. Add about 3.6 liters of absolute methanol and stir until the alcohol is absorbed into the paste. Transfer the mixture to a large vacuum filter, and remove as much of the liquid as possible with or without the use of an implement such as a rubber dam. Transfer the solid filter cake to the stainless steel mixer and add about 3.6 liters of fresh absolute methanol and stir until the alcohol is absorbed. Transfer this mixture again to the vacuum filter to remove the filtrate. A total of about 4 washings results in a product free of water, mono- and tribenzylidene-D-sorbitols, alkaline impurities and acid catalyst as determined by HPLC and hardness of a gel stick made by the product. After the final wash, break the filter cake into small pieces and allow it to air dry for about 24 hours. Grind the pieces and air dry to a constant weight. This results in a 77% yield or about 933.08 grams of di-(meta-fluorobenzylidene)-D-sorbitol fully characterized by $^1$H NMR, $^{13}$C NMR and mass spectral analysis.

$^1$H NMR (300 MHz, DMSO-$d_6$) (ppm) 3.405–3.500 (5 peak m, 1H), 3.580–3.670 (7 peak m, 1H), 3.740–3.805 (6 peak m, 1H), 3.850–3.900 (2 peak m, 1H), 3.950(s, 1H), 4.150–4.205 (2 peak m, 2H), 4.460–4.520 (t, 1H, exchanges in the presence of acid, CH$_2$O$\underline{H}$), 4.940–4.980 (d, 1H, exchanges in the presence of acid, CH$_2$O$\underline{H}$), 5.750 (s, 2H, benzylic H), 7.250–7.510 (8 peak m, 10$\underline{H}$, aromatic). $^{13}$C NMR (DMSO-$d_6$) (ppm) 62.92–63.01 (2 peaks, CH$_2$), 67.95–68.04 (2 peaks, CH), 68.81 (CH), 69.66 (CH$_2$), 70.46 (CH), 77.89 (CH), 98.53–98.58 (2 peaks, CH), 113.10–113.40 (3 peaks, CH), 115.62115.98 (4 peaks, CH), 122.53–122.59 (2 peaks, CH), 130.45–130.66 (3 peaks, CH), 141.38–141.73 (4 peak, quat, ipso C), 160.69 (s, quat, CF), 163.91 (s, quat, CF). MS: Calcd. for $C_{20}H_{20}F_2O_6$, 394. Obs. MH+395.

EXAMPLE II

Preparation of di-(meta-chlorobenzylidene)-D-sorbitol

Add 18.22 g of D-sorbitol, 23.63 g of para-toluenesulfonic acid monohydrate, and 100 ml of absolute methanol to a round bottom flask equipped with a stirrer, thermometer and heating mantle. With stirring, heat the mixture to about 40° C. and add 25.3 g of 3-chlorobenzaldehyde to the flask. Continue stirring at room temperature for about 20 hours until the mixture forms a thick paste. Add about 200 ml of absolute methanol and stir until all the methanol is absorbed. Transfer the mixture to a vacuum filter and remove as much of the liquid as possible. Transfer the solid to a beaker and add about 200 ml of fresh absolute methanol. Stir until all the methanol is absorbed. Transfer this mixture again to the vacuum filter to remove filtrate. A total of about 5 washings results in a product substantially free of water, mono- and tribenzylidene-D-sorbitols, alkaline impurities, and acid catalyst as determined by HPLC and hardness of the gel stick made from the product. After the final wash, break the filter cake into pieces and air dry for about 24 hours. Grind these pieces to a powder and air dry to a constant weight. This results in about a 48% yield or 18.29 grams of di-(meta-chlorobenzylidene)-D-sorbitol.

EXAMPLE III

Preparation of di-(meta-bromobenzylidene)-D-sorbitol

With stirring, add 2.73 g of D-sorbitol, 5.0 g of 3-bromo-benzaldehyde and 50 ml of absolute methanol in a round bottom flask equipped with a thermometer and heating mantle. Add 3.61 g of para-toluenesulfonic acid monohydrate to the flask and heat to about 30° C. Continue stirring at room temperature for about 48 hours or until the mixture forms a thick paste. Add about 100 ml of fresh absolute methanol to the paste and stir until all the methanol is absorbed. Transfer this mixture to a vacuum filter and remove as much of the liquid as possible. Transfer the solid to a beaker and add 100 ml of fresh absolute methanol. Stir until all the methanol is absorbed and filter as disclosed above. A total of about 3 washings results in a product substantially free of water, mono- and tribenzylidene-D-sorbitols, alkaline impurities, and acid catalyst as determined by HPLC and hardness of the gel stick made from the product. After the final wash, break the filter cake into pieces and air dry for about 24 hours. Grind these pieces and dry to a constant weight. This results in about a 53% yield or 3.66 grams of di-(meta-chlorobenzylidene)-D-sorbitol.

EXAMPLE IV

Preparation of di-(meta-fluorobenzylidene)-D-sorbitol

With stirring, add 8.1 kg of D-sorbitol, 10.0 kg of 3-fluorobenzaldehyde, and about 36 l of methanol in a 40 gallon, stainless steel, double blade planetary mixer. Add 10.6 kg of para-toluenesulfonic acid monohydrate to the mixer and continue stirring for about 20 hours until the mixture forms a thick paste. Add about 64 l of fresh absolute methanol to the paste and stir until the methanol is absorbed. Transfer the mixture to a vacuum filter or filters and remove as much of the liquid as possible. Transfer the solid to the stainless mixer and add about 64 l of fresh absolute methanol. Stir until the methanol is completely absorbed and filter as disclosed above. A total of about 6 washings results in a product substantially free of water, mono- and tribenzylidene-D-sorbitols, alkaline impurities, and acid catalyst as determined by HPLC and hardness of the gel stick made from the product. After the final wash, break the filter cake(s) in pieces and air dry for about 24 hours. Grind these pieces and dry to a constant weight. This results in about an 75% yield or 11.8 kg of di-(meta-fluorobenzylidene)-D-sorbitol.

EXAMPLE V

Preparation of dibenzylidene-D-sorbitol

Add 310 g of D-sorbitol and 1 l of absolute methanol in a 2 gallon, stainless steel, double blade planetary mixer and stir for about 10 minutes. Add 315 g of benzaldehyde and 405 g of paratoluenesulfonic acid monohydrate to the mixer and continue stirring for about 5 hours until the mixture forms a thick paste. Add about 3 l of fresh absolute methanol and stir until absorbed into the paste. Transfer this mixture to a vacuum filter and remove as much liquid as possible. Transfer the solid to the stainless steel mixer and add 3 l of fresh absolute methanol. Stir until the methanol is absorbed and filter as disclosed above. A total of about 3 washings results in a product substantially free of water, mono- and tribenzylidene-D-sorbitols, alkaline impurities, and acid catalyst as determined by HPLC and hardness of the gel stick made from the product. After the final wash, break the filter cake into pieces and air dry for about 24 hours. Grind these pieces and dry to a constant weight. This results in about a 57% yield or 270.8 grams of dibenzylidene-D-sorbitol fully characterized by $^1$H NMR, $^{13}$C NMR and mass spectral analysis. $^1$H NMR (500 MHz, DMSO-$d_6$) (ppm) 3.394–3.470 (5 peak m, 1H), 3.571–3.626 (7 peak m, 1H), 3.745–3.796 (6 peak m, 1H), 3.821–3.852 (2 peak m, 1H), 3.908(s, 1H), 4.138–4.143 (2 peak m, 2H), 4.397–4.436 (t, 1H, exchanges in the presence of acid, CH$_2$O$\underline{H}$), 4.832–4.851 (d, 1H, exchanges in the presence of acid, CHO$\underline{H}$), 5.638 (s, 2H, benzylic H), 7.336–7.476 (10 peak m, 10$\underline{H}$, aromatic). $^{13}$C NMR (DMSO-$d_6$) (ppm) 63.06 (CH$_2$), 68.14 (CH), 68.85 (CH), 69.75 (CH$_2$), 70.51 (CH), 78.05 (CH), 99.71 (CH), 126.48 (CH), 126.66 (CH), 128.36 (CH), 129.01 (CH), 138.90 (quat), 139.15 (quat).

MS: Calcd. for $C_{20}H_{22}O_6$, 358. Obs. MH+359.

What is claimed is:

1. A process for making a dibenzylidene-D-sorbitol compound, consisting essentially of the steps of:
   a. combining D-sorbitol, an aromatic aldehyde, an acid catalyst and a $C_1$-$C_3$ aliphatic alcohol reaction medium;
   b. allowing the mixture to form a thick paste; and
   c. washing said mixture with a $C_1$-$C_3$ aliphatic alcohol until the compound formed is substantially free of the acid catalyst;

wherein the initial molar ratio of aromatic aldehyde to D-sorbitol is from about 1:1 to about 2:1, the initial molar ratio of acid catalyst to aromatic aldehyde is from about 0.6:1 to about 1.5:1.

2. A process according to claim 1 wherein the aromatic aldehyde is substituted at the 3 position by hydrogen, fluorine, chlorine or bromine.

3. A process according to claim 2 wherein the aromatic aldehyde is selected from the group consisting of benzaldehyde, 3-fluorobenzaldehyde, 3-chlorobenzaldehyde, 3-bromobenzaldehyde, and mixtures thereof.

4. A process according to claim 3 wherein the $C_1$-$C_3$ aliphatic alcohol is selected from the group consisting of methanol, ethanol, isopropanol, and mixtures thereof.

5. A process according to claim 4 wherein the acid catalyst is selected from the group consisting of para-toluenesulfonic acid monohydrate, benzenesulfonic acid, 5-sulfosalicylic acid, naphthalenesulfonic acid, and mixtures thereof.

6. A process according to claim 5 wherein the aromatic aldehyde is 3-fluorobenzaldehyde.

7. A process according to claim 4 wherein the $C_1$-$C_3$ aliphatic alcohol is methanol.

8. A process according to claim 5 wherein the acid catalyst is para-toluenesulfonic acid monohydrate.

9. A process according to claim 8 wherein the molar ratio of aromatic aldehyde to D-sorbitol is from about 1.5:1 to about 1.9:1.

10. A process according to claim 9 wherein the molar ratio of aromatic aldehyde to D-sorbitol is from about 1.7:1 to about 1.8:1.

11. A process according to claim 9 wherein the molar ratio of acid catalyst to aromatic aldehyde is from about 0.6:1 to about 1:1.

12. A process according to claim 10 wherein the molar ratio of acid catalyst to aromatic aldehyde is about 0.7:1.

13. A process according to claim 1 wherein the initial weight ratio of $C_1$-$C_3$ aliphatic alcohol reaction medium to D-sorbitol is from about 2:1 to about 15:1.

14. A process according to claim 13 wherein the initial weight ratio of $C_1$-$C_3$ aliphatic alcohol reaction medium to D-sorbitol is about 2.5:1 to about 3:1.

15. A process according to claim 1 wherein the reaction product is not subjected to a neutralization step.

16. A process according to claim 1 wherein the dibenzylidene-D-sorbitol compounds formed are substantially free of water, mono- and tribenzylidene sorbitols, alkaline impurities, and acid catalyst.

* * * * *